(12) United States Patent
Ruoss et al.

(10) Patent No.: US 7,196,629 B2
(45) Date of Patent: Mar. 27, 2007

(54) RADAR-ASSISTED SENSING OF THE POSITION AND/OR MOVEMENT OF THE BODY OR INSIDE THE BODY OF LIVING BEINGS

(75) Inventors: Hans-Oliver Ruoss, Stuttgart (DE); Michael Mahler, Leinfelden-Echterdingen (DE); Juergen Seidel, Pluederhausen (DE)

(73) Assignee: Robert Bosch GmbH, Stuttgart (DE)

( * ) Notice: Subject to any disclaimer, the term of this patent is extended or adjusted under 35 U.S.C. 154(b) by 2 days.

(21) Appl. No.: 10/497,870

(22) PCT Filed: Oct. 23, 2003

(86) PCT No.: PCT/DE03/35319

§ 371 (c)(1),
(2), (4) Date: Jun. 7, 2004

(87) PCT Pub. No.: WO2004/057367

PCT Pub. Date: Jul. 8, 2004

(65) Prior Publication Data

US 2005/0073424 A1 Apr. 7, 2005

(30) Foreign Application Priority Data

Dec. 19, 2002 (DE) ............... 102 59 522

(51) Int. Cl.
*B60Q 1/00* (2006.01)
*G08B 13/00* (2006.01)
*G08B 21/00* (2006.01)
*G08B 23/00* (2006.01)
*B60R 21/16* (2006.01)
*G01S 13/00* (2006.01)
*G01S 13/08* (2006.01)

(52) U.S. Cl. ............ 340/573.1; 340/574; 340/575; 340/576; 340/686.6; 340/436; 340/437; 340/438; 280/734; 280/735; 342/61; 342/118

(58) Field of Classification Search .......... 340/573.1, 340/686.6, 574–576, 436–438; 342/61, 118, 342/70–72; 128/653, 663, 687; 280/734–735
See application file for complete search history.

(56) References Cited

U.S. PATENT DOCUMENTS 3,911,899 A * 10/1975 Hattes .................. 600/407

(Continued)

FOREIGN PATENT DOCUMENTS

WO        00 58584 A      10/2000

(Continued)

*Primary Examiner*—Daniel Wu
*Assistant Examiner*—Lam Pham
(74) *Attorney, Agent, or Firm*—Michael J. Striker (57) ABSTRACT

The present invention relates to a method for sensing information about the position and/or movements of the body of a living being or a part of the body inside the body, in particular for use in a motor vehicle. The method includes the steps:
  Send (18) an electromagnetic signal (15) that includes, according to the invention, frequencies in the radar range, to a predetermined area of the body of a living being,
  Receive (20) an electromagnetic signal (22) reflected from the area of the body,
  Evaluate (30) the captured receive signal (22) with regard for the difference in delay time and/or frequency relative to the transmit signal (15) to determine the information.
With the method according to the present invention, the breathing and heart rate and the position of the body of a driver of a motor vehicle can be monitored in contactless fashion during the drive.

15 Claims, 5 Drawing Sheets

U.S. PATENT DOCUMENTS

| | | | |
|---|---|---|---|
| 4,217,582 A * | 8/1980 | Endo et al. | 342/70 |
| 4,513,748 A * | 4/1985 | Nowogrodzki et al. | 600/453 |
| 4,706,072 A * | 11/1987 | Ikeyama | 340/576 |
| 5,141,308 A * | 8/1992 | Danckwerth et al. | 356/5.05 |
| 5,760,687 A * | 6/1998 | Cousy | 340/554 |
| 5,790,032 A | 8/1998 | Schmidt | |
| 5,848,802 A * | 12/1998 | Breed et al. | 280/735 |
| 5,904,368 A * | 5/1999 | Blackburn et al. | 280/735 |
| 6,104,296 A * | 8/2000 | Yasushi et al. | 340/576 |
| 6,252,240 B1 * | 6/2001 | Gillis et al. | 250/559.38 |
| 6,254,127 B1 | 7/2001 | Johnson | |
| 6,275,146 B1 * | 8/2001 | Kithil et al. | 340/425.5 |
| 6,290,255 B1 * | 9/2001 | Stanley et al. | 280/735 |
| 6,359,597 B2 * | 3/2002 | Haj-Yousef | 343/850 |
| 6,661,345 B1 * | 12/2003 | Bevan et al. | 340/575 |
| 6,820,897 B2 * | 11/2004 | Breed et al. | 280/735 |
| 6,822,573 B2 * | 11/2004 | Basir et al. | 340/575 |
| 7,088,250 B2 * | 8/2006 | Yasushi | 340/573.1 |

FOREIGN PATENT DOCUMENTS

WO      03 019236 A      3/2003

* cited by examiner

RADAR-ASSISTED SENSING OF THE POSITION AND/OR MOVEMENT OF THE BODY OR INSIDE THE BODY OF LIVING BEINGS

BACKGROUND OF THE INVENTION

The present invention is directed to a method for sensing information about the position and/or movements of the body of a living being or a part of the body inside the body.

There is a great deal of interest in methods for detecting such information not only in the field of medical technology but also in the automotive industry in particular, because inattentiveness, falling asleep at the wheel and cardiac stress caused by stressful situations are frequent causes of accidents with fatalities. For this reason, various approaches are taken to detect physiological measurement parameters such as the heart beat, breathing and the position of the body. These parameters are evaluated and, depending on the results, warning signals can be generated. This information can be used to characterize the driver's state, or as data to control the triggering of an airbag, for example.

Optical measurement methods with cameras are known in the related art for detecting the position and movements of the body. Image evaluation is difficult and requires a large amount of evaluation logic, however, which results in higher costs. In addition, it is unable to determine movements inside the body, e.g., the heart beat.

Electrocardiography is used to observe such movements inside the body, of the heart, in particular. Methods used in electrocardiography have the disadvantage, however, that they are not contactless, because electrodes must be placed on the body.

Infrared measurements are also unsuitable for the purposes stated above, due to their inaccuracy and poor resolution for observing processes inside the body.

A method of measuring the position and/or movements of the body, primarily inside the body as well, that is free from drawbacks and sufficiently free from interference, and that is desired in automotive technology in particular, has not yet been found for use outside of test conditions.

SUMMARY OF THE INVENTION

With the measures of the independent claims, the advantage is attained of being able to detect the position and/or movements of a body or in a body in a targeted and contactless manner, i.e., without electrical contact with the body of the living being, and, with little outlay for material and programming logic, to process it further and forward it to higher-order systems, if necessary. The required transmitting power of approx. 1 mW is far below the international limiting value for personal safety. The method according to the invention may be used in motor vehicles in particular.

The present invention is based on the knowledge—explained hereinbelow—of the interaction of the body of a living being with electromagnetic waves from the high-frequency range, in particular the radar frequency range: The body is composed of numerous different types of tissue. Each tissue type has different electrical properties (i.e., electrical conductivity, dielectric constants, penetration depth for electromagnetic fields, etc.). Due to these differences, jumps in the properties occur at the transition points, i.e., the "points of impact". Said jumps result in a portion of penetrating electromagnetic waves from the high-frequency range being reflected.

Said reflections are capable of being utilized particularly well to measure heart beat and breathing. The tissue differences between the layers over the heart (fat/muscle and muscle/bone, . . . ) are small, so that hardly any reflections of electromagnetic waves take place there. In contrast, a stronger reflection is obtained when the wave impacts the heart, because the difference here, namely between blood and heart tissue, is particularly great. Due to this strong reflection, it is possible to determine the position of this "point of impact" over time. The change of position and shape of the heart in the chest over time generates a Doppler shift of the reflected electromagnetic wave, with the aid of which the heart beat can be measured.

Due to the anatomical structure, the wave is reflected not only at a (selective) point of impact in the heart, however. Reflections at various areas of the heart (e.g., at the heart valves) take place, because the heart is an organ that is well supplied with blood and through which blood flows. The strong reflection at the "blood/tissue" junction mentioned above applies for all of these sites. The signal intensity here depends on the penetration depth of the tissue types and the measurement depth, however.

Depending on the position of the transmit/receive antenna elements with the method according to the invention, other penetration depths to the heart result. These distances influence the signal quality and signal form. The signal form is predetermined by the point of impact, because each point in the heart has a different spatial sequence of movements.

The heart beat can be characterized with the present invention. With the sensor according to the invention, it is possible to determine and physiologically interpret not only the pulse frequency, but also the "pumping motion" of the heart.

To measure breathing, a further strong reflection at the outer region/chest cavity junction is utilized. This signal is determined using the same method according to the invention. As a result, it is possible to simultaneously measure breathing and heart beat with the method according to the invention.

Advantageous embodiments, further developments and improvements of the particular object of the invention are indicated in the subclaims.

In an advantageous manner according to the invention, movements of the body or parts of the body inside the body may be determined by evaluating the receive signal and transmit signal by determining the Doppler frequency shift between the two signals. This is a simple and sufficiently accurate method for determining bodily movements.

Preferably, the method according to the invention is designed for radar frequencies in the range between 800 to 5 GHz and, in particular, for a frequency band of 100 MHz around 2.45 GHz. Electromagnetic waves in this frequency range are particularly well-suited to detection of bodily movements, primarily due to the adequate penetration depth. Furthermore, special approval is not required for frequencies from the ISM band of 100 MHz around 2.45 GHz.

The method according to the invention can be developed further in advantageous fashion with a signal serving as an alarm that is triggered when the evaluated physiological measured data indicate a life-threatening, extraordinary situation. Situations of this nature can be cardiac infarct, cardiac arrhythmia, or cessation of breathing, for example.

Another advantage is the embodiment of the present invention such that the radar field is a pulsed field. As a result, the distance d between body and transmit/receive antenna elements may be monitored based on the difference in delay time between transmit and receive signal. This is beneficial for controlling the triggering of an airbag, for example. Preferably, this method can be designed for frequencies in the range between 20 to 120 GHz and, in particular, in the frequency band of 250 MHz around 24.5 GHz. With such high frequencies, the time difference for determining distance may be determined very accurately. In addition, the radar waves in this frequency range barely penetrate the body; instead, they are largely reflected on the surface. As a result, the measured data for the instantaneous position and movement of a point on the body surface are particularly exact and distinct.

The short radar pulses are generated in an advantageous manner either by a switching on and off using a clock-pulse generation circuit that triggers a signal switch, or by a signal filter of the clock-pulse signal.

The evaluation of the received electromagnetic waves is preferably carried out either according to the sampling principle by selectively sampling the signal, or according to the more economical mixing principle, with which a branched-off portion of the transmit signal (reference signal) is compared with the receive signal and the information resulting therefrom is analyzed to determine the bodily movement. An I/Q arrangement can be used to prevent evaluation problems with zero values of the mixed signal. A signal evaluation arrangement of this type is characterized by the fact that a further channel in which the reference signal is phase-shifted by 90 degrees is used, and by the fact that the complex amplitude of the mixed signal is determined in the sum of the two signal outputs downstream of the two paths.

The system that contains devices for carrying out the steps according to one of the methods according to the invention can be applied preferably to monitor the driver or passenger, and to determine the presence of a living being in the trunk of a motor vehicle. The information obtained therewith can be used, in particular, to monitor the health of the driver, the control of the triggering of an airbag, and to unlock the trunk in the case of emergency.

BRIEF DESCRIPTION OF THE DRAWINGS

Exemplary embodiments of the invention are explained with reference to the drawings.

DETAILED DESCRIPTION OF THE PREFERRED EMBODIMENTS

In the figures, the same reference numerals label components that are the same or that have the same function.

Figure 1:
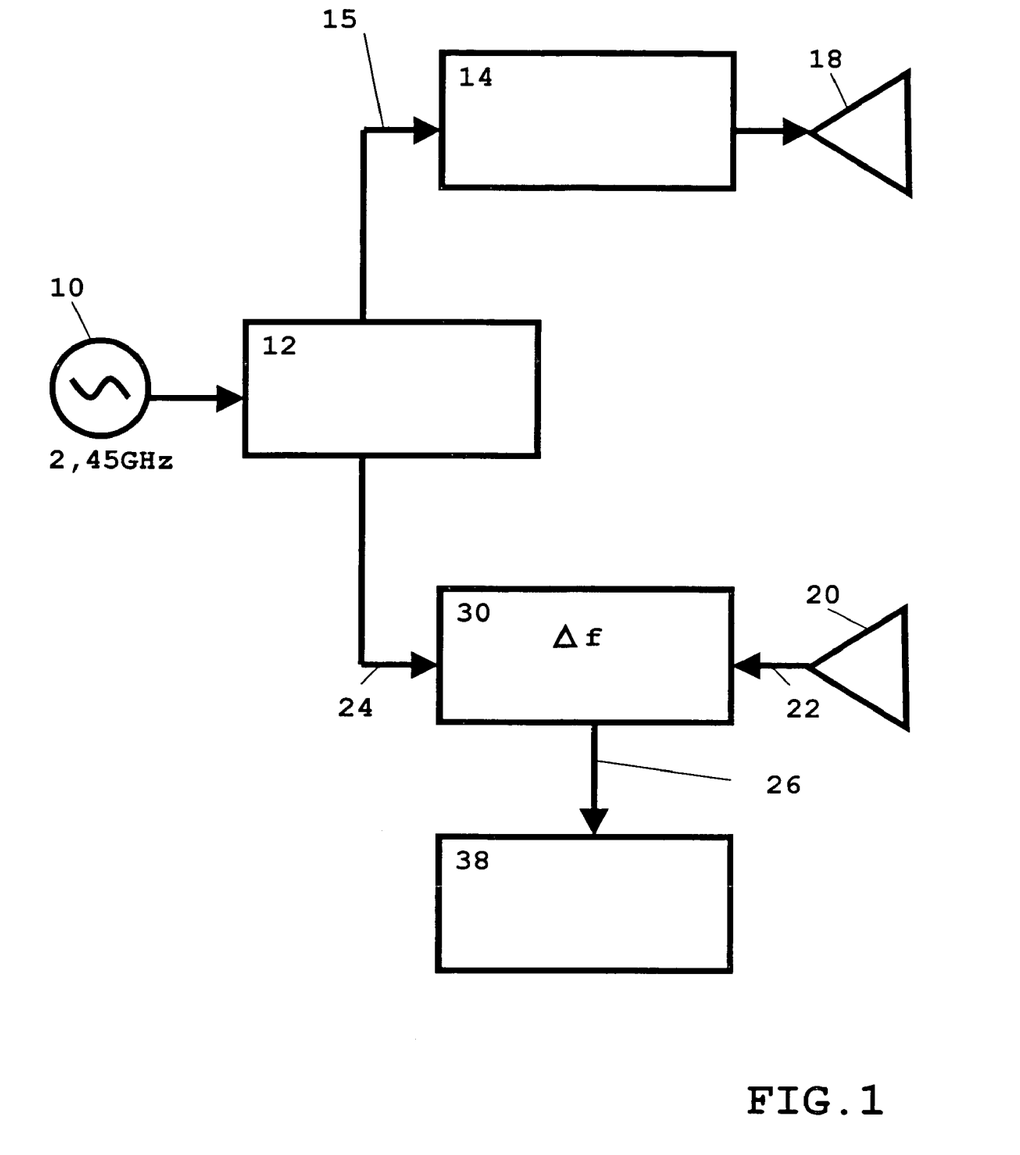
FIG. 1 shows a block diagram of the configuration of a system for sensing according to the method according to the invention in the embodiment of a continuous wave (CW) radar.

FIG. 1 shows a block diagram of the configuration of a system for sensing according to the method, according to the invention, in the embodiment of a continuous wave (CW) radar. With continuous wave radar, continuous—instead of pulsed—electromagnetic waves are used in the radar frequency range.

A high-frequency, continuous useful signal in the GHz range having a frequency, e.g., of 2.45 GHz and average power of approximately 1 mW is conducted from a frequency generator 10, type VCO, to a 3 dB power divider 12. The signal is split into a transmit signal 15 and a reference signal 24 in a 1:1 ratio. Transmit signal 15 travels via a band pass filter 14, which filters out all frequencies outside the ISM band (2.45 GHz+/−50 MHz), to radar transmit antenna 18. From there, a continuous electromagnetic wave is emitted in the direction of the area of the body site to be observed. Transmit antenna 18 is installed in the steering wheel of a motor vehicle, for example, whereby the radar wave is directed toward the driver's chest region; refer also to FIG. 7. The radar waves that are reflected at the points of impact with the body, in particular at the chest surface and the cardiac wall, are captured by receive antenna 20, which is also located in the steering wheel, for example. Receive signal 22, which is forwarded by antenna 20, reaches signal evaluation device 30, into which reference signal 24 is also directed. The signal depicting the desired movement information is output at signal output 26 of evaluation device 30 and forwarded to an alarm signal generator 38. If the heart beat exceeds or falls below a certain frequency, or if the heart rhythm exhibits an unusual change, an acoustic or optical alarm signal is produced in said alarm signal generator, or the information is forwarded to a higher-order system.

Figure 2:
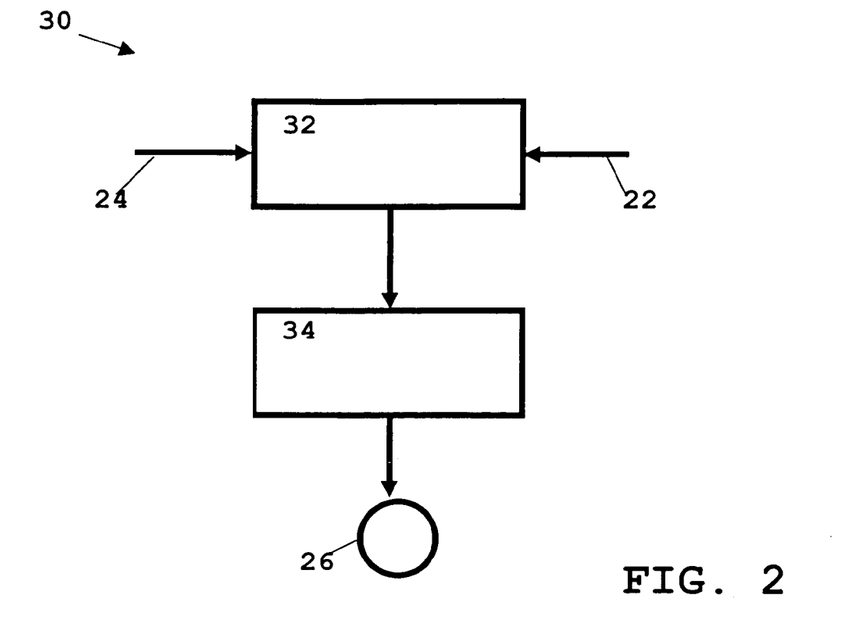
FIG. 2 shows a block diagram of a configuration of a variant of signal evaluation according to the mixer principle as a component of a system according to an embodiment of the method according to the invention.
Figure 3:
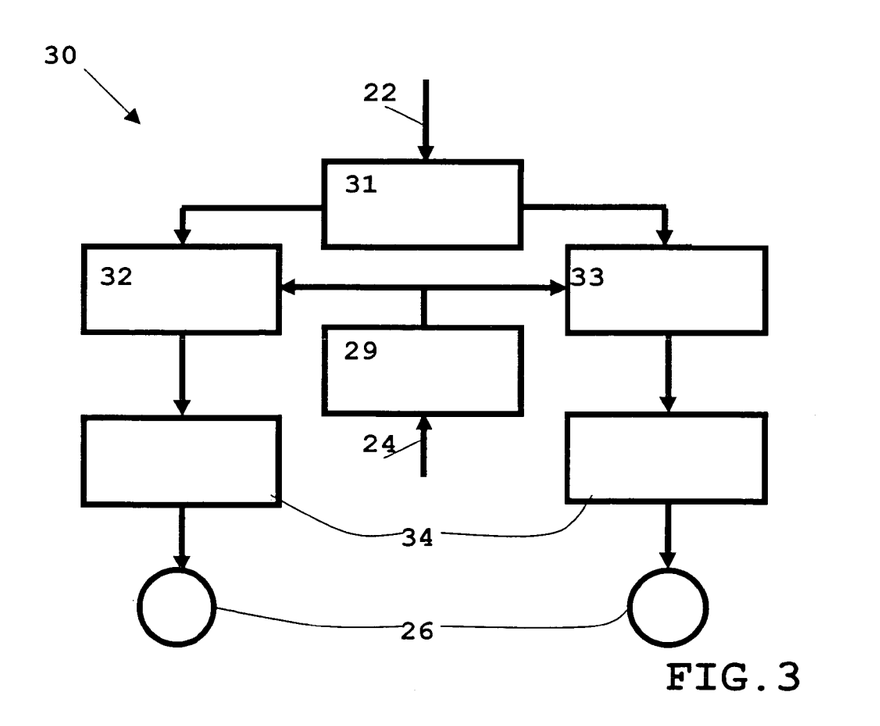
FIG. 3 shows a block diagram of a configuration of a further variant of the signal evaluation according to the mixer principle as a component of a system according to an embodiment of the method according to the invention.

According to the invention, various embodiments are provided for signal evaluation device 30. Two examples are depicted in FIGS. 2 and 3. Both of them are based on the mixer principle, with which receive signal 22 and reference signal 24 are superposed and—in accordance with the mixer principle—"composite" and/or "differential" signals are generated.

FIG. 2 shows the simpler embodiment of a signal evaluation device 30 of this nature. Receive signal 22 and reference signal 24 reach signal mixer 32, in which the signals are correlated. Signal mixer 32 is equipped with a band pass filter to suppress the interfering secondary signals-undesired mixed products, but also the 50 Hz interfering signal, for example. From the signal mixer, the resultant mixed signal is directed to a further band pass filter 34 with built-in amplifier, which selectively allows only the frequencies required to determine the movement information to pass through, and amplifies them. Said frequencies are the Doppler frequencies and their changes over time in the frequency shift from receive signal to reference signal. The frequency for the changes in Doppler frequencies is 0.01 to 0.5 Hz in the case of the movement of the chest cavity that occurs with breathing, for example, and in the range of 0.5 to 3 Hz for the heart rate. The Doppler frequencies for successful signal evaluation, on the other hand, are in the frequency range up to 20 Hz. At signal output 26, the signals that are allowed to pass through and are amplified in this manner are output to depict the desired movement information.

FIG. 3 shows an expanded form of a signal evaluation device 30 according to the mixer principle. This "I/Q evaluation" essentially contains two instead of one signal mixer 32. Receive signal 22 and reference signal 24 are each distributed through a 3 dB power divider 29, 31 in a 1:1 ratio to the two mixers 32 and 33. In addition, the part of receive signal 22 forwarded to the one mixer 33 is phase-shifted by 90 degrees in power divider 31. As described for FIG. 2, the resultant signal is then generated in each of the two mixers 32 and 33 and further, the frequencies required to determine the movement are selected and amplified via band pass filter 34 with amplifier. With the signals output at the two signal outputs 26, the complex amplitude of the entire output signal can be used to depict the movement information. As a result, evaluation problems with zero values of the one mixed signal can be prevented.

Figure 4:
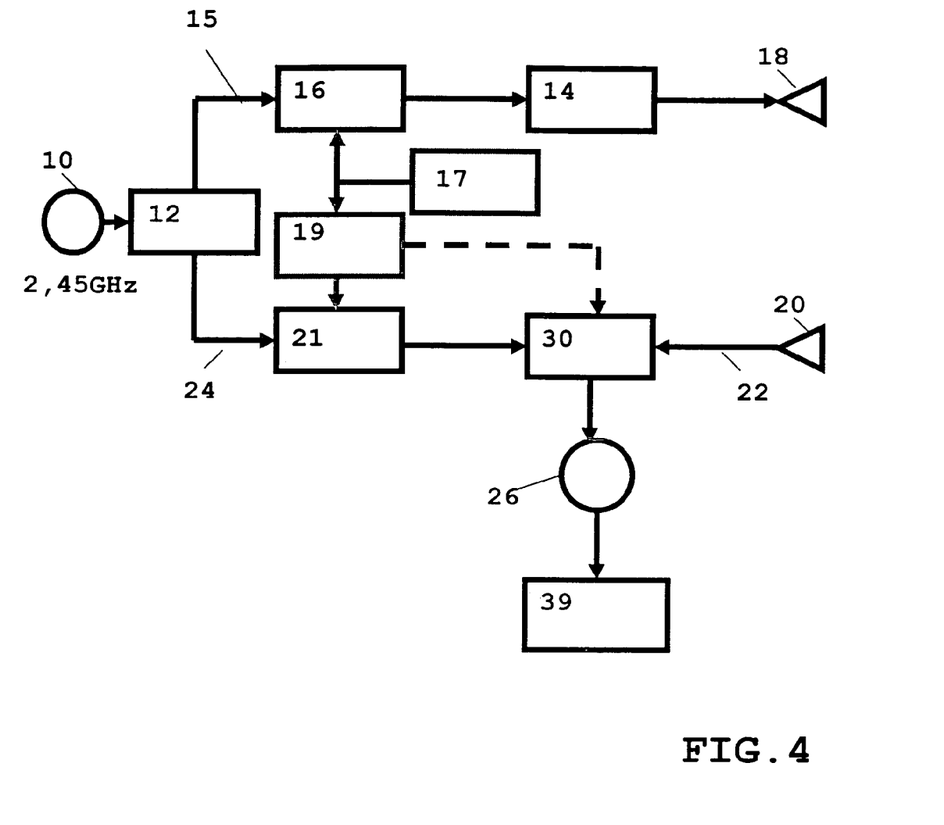
FIG. 4 shows a block diagram of a configuration of a system for sensing according to the method according to the invention, in an embodiment of an impulse radar.

FIG. 4 shows a block diagram of a configuration of a system for sensing according to the method according to the invention in an embodiment of an impulse radar. This is a radar system with which pulsed electromagnetic waves are used.

A high-frequency useful signal with a frequency of, e.g., 2.45 GHz is conducted from frequency generator 10, type VCO, to a 3 dB power divider 12. The signal is divided into a transmit signal 15 and a reference signal 24 in a 1:1 ratio. Transmit signal 15 further reaches a very fast p-i-n diode switch 16, which allows transmit signal 15 to pass only in short pulses (1 to 10 ns pulse length).

Switch 16 is regulated using a control signal that comes from a control signal generator 17. For example, control signal generator 17 can deliver an impulse with the length of the switching duration.

Transmit signal pulses 15 are directed to radar transmit antenna 18 via a band pass filter 14 that filters out all frequencies outside the ISM band (2.45 GHz+/−50 MHz). From there, electromagnetic wave pulses 15 are emitted in the direction of the region of the body site to be observed. Transmit antenna 18 is installed in the steering wheel of a motor vehicle, for example, whereby the radar wave is directed at the driver's chest region.

The radar wave pulses reflected at the point of impact of the body, in particular at the chest surface and the cardiac wall, are captured by receive antenna 20, which is located in the steering wheel, for example. Pulsed receive signal 22, which is forwarded from antenna 20, reaches signal evaluation device 30, into which reference signal 24 is also directed. Reference signal 24 that arrives there is also pulsed, which is carried out by switch 21.

Said switch 21 is coupled with switch 16 in such a manner that it is triggered via control signal generator 17 via the same control signal, but with an added variable time delay 19.

Delay element 19 carries out the time delay; for example, the delay element moves the instant for the opening signal backward piece-by-piece, moving up the spikes of the sawtooth voltage of control signal generator 17. As a result, the pulses of reference signal 24 are delayed accordingly relative to those of the transmit signal.

A superimposition of reference pulse 24 and receive pulse 22 in signal evaluation 30 that is necessary for the result signal at signal output 26 is achieved with a time delay of reference pulse 24 that corresponds to the delay time of the emitted and reflected radar wave. The value of this delay is transmitted by delay element 19 to evaluation device 30, and is used as information for the distance d (refer to FIG. 7) between the body or body part and the transmit and/or receive antenna 18, 20. The signal evaluation with regard for bodily movements takes place according to the methods described for FIGS. 2 or 3, for example. The result at signal output 26 is forwarded via wireless data transmission to a higher-order system 29 for further processing, in the manner of a medical evaluation, for example.

Figure 5:
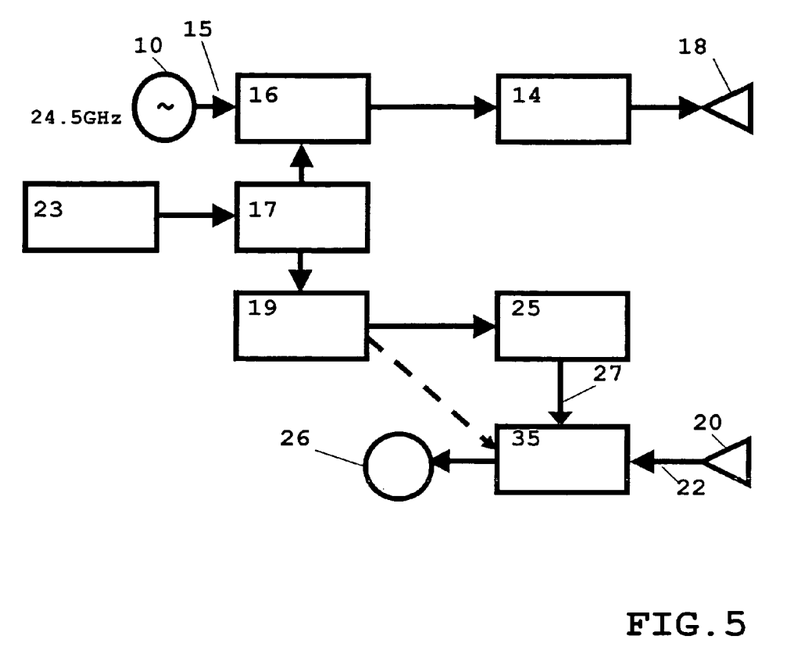
FIG. 5 shows a block diagram of a configuration of a system for sensing according to the method according to the invention in a further embodiment of an impulse radar.
Figure 6:
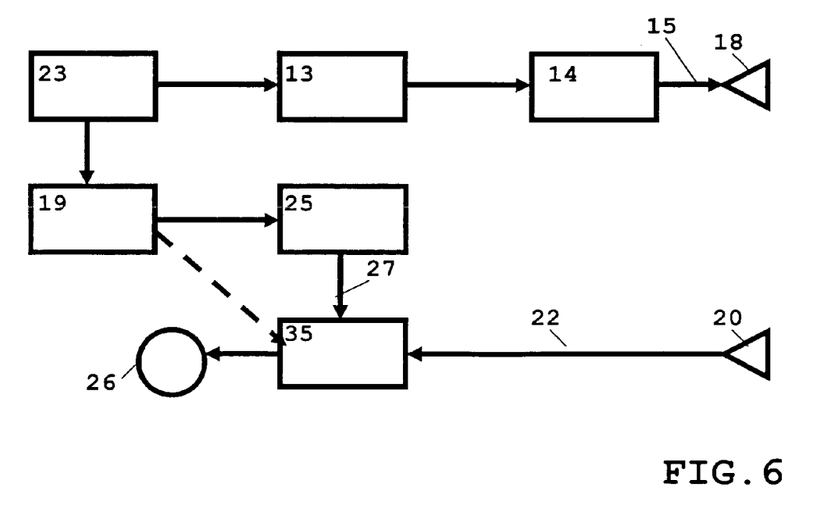
FIG. 6 shows a block diagram of a configuration of a system for sensing according to the method according to the invention in a further embodiment of an impulse radar.

Another signal evaluation method that is also suitable is the sampling principle illustrated with FIGS. 5 and 6, with which receive signal 22 is sampled in sample clock steps.

In the variant depicted in FIG. 5, a high-frequency useful signal with a frequency of, e.g., 24.5 GHz from a high-frequency generator 10 is used for the transmit signal frequency. Pulsed with the aid of switch 16 and filtered through band pass filter 14, transmit signal 15 is emitted by antenna 18 as a radar wave pulse, and the part reflected at the points of impact is received with receive antenna 20. The control of switch 16 is carried out using a control signal generated in control signal generator 17. The clock timing generator for this signal is a clock pulse generator 23, such as a commercially available clock for high frequencies.

Furthermore, control pulse generation 25, in addition to switch 16, is regulated for sampling by the signal from control signal generator 17. However, a varying time delay is built into this control via an interconnected delay element 19 to compensate for the delay equalization. The value of the delay is transmitted to antenna elements 18 and 20 on sampler 35 to determine distance d (refer to FIG. 7). (Since the receive signal is sampled constantly, the signal is practically already AND converted. The delay time can be calculated by comparing the receive signal with the transmit signal, thereby determining the time difference.)

With control pulse 27 that is then generated in sampling control pulse generator 25, sampler 35 that samples receive signal 22 is controlled. The resultant sampling data are then output at signal output 26 of sampler 35 for information analysis.

In the alternative depicted in FIG. 6, the clock signal of clock pulse generator 23 of sampling pulse control 25 is used instead of a separate, high-frequency useful signal as the basis for transmit pulse 15. With this clock signal, short pulses are generated using a pulse generator 13, which can be a diode, for example, out of which said pulses the corresponding part of their Fourier spectrum—which has been widened by the shortness of the pulse—is allowed through as transmit pulse 15 in the downstream band pass filter 14. In this manner, the ISM band can be used for the radar pulse frequencies, for example. For more exact distance measurements, the frequency band around 24.5 GHz—which is located ten times higher—can also be used.

Figure 7:
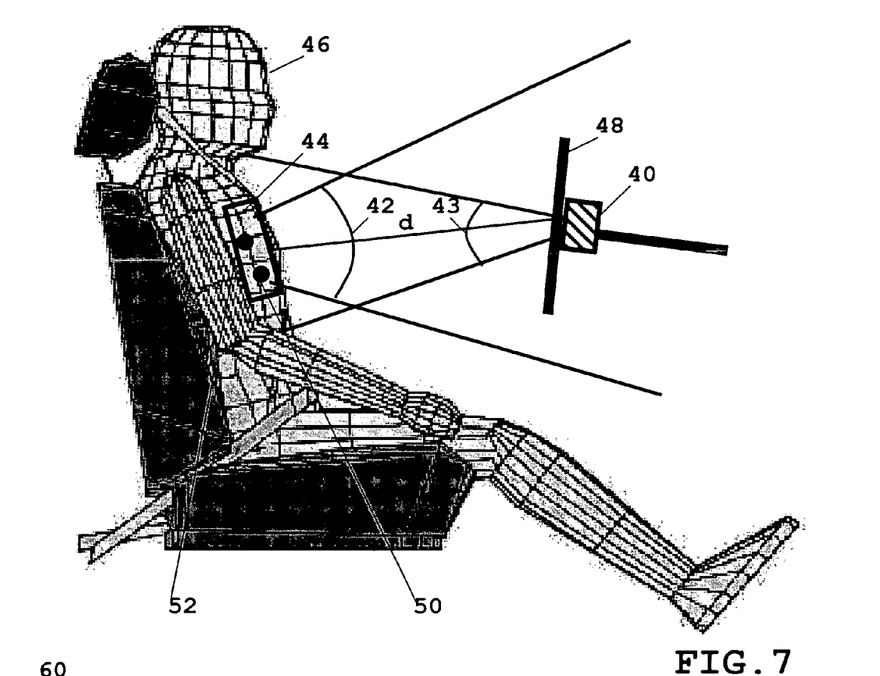
FIG. 7 shows, schematically, in a lateral cross-section, a sensor device with sensor region for the method according to the invention in a motor vehicle.

In FIG. 7, a sensor device 40 with sensor region for the method according to the invention is depicted schematically in a motor vehicle in a lateral cross section. Sensor device 40 according to the invention is mounted in a location in the permitted angular range 42 in front of chest section 44 of driver 46. A suitable position within angular range 42 with an aperture of approximately 30 degrees would be in steering wheel 48, for example. The electromagnetic wave can be directed toward heart 50 and/or measuring range 52 of breathing motion. In addition to the heart beat and breathing motion, distance d between person 46 and sensor 40 is also measured. Its emission characteristics have an angle of aperture 43 of up to 45 degrees.

The control and evaluation elements for sensor 40 can be located in another location in the motor vehicle, such as in the center console.

Figure 8:
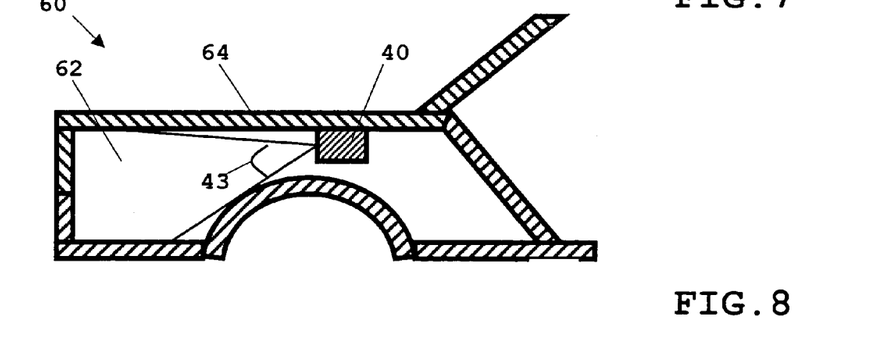
FIG. 8 shows, schematically, in a lateral cross-section, a sensor device with sensor region for the method according to the invention in the trunk of a motor vehicle.

FIG. 8 shows a schematic depiction of a sensor device 40 for the method according to the invention in trunk 62 of a motor vehicle 60 in a lateral cross section. Sensor 40 is mounted under trunk lid 64 in such a manner that the observation range in transmission aperture 43 covers the majority of trunk 62. As a result, it can be determined whether a living being is located therein. This can be used to automatically open the door in case of an accident.

A radar-based sensor 40 for determining heart beat and breathing rate can be used with great benefit in the following tasks and/or systems in a motor vehicle:

Detecting the presence of a person: By measuring heart rate (based on the seated position), a distinction can be made between a person who is present and an object. A system of this nature can support the triggering of an airbag. If an airbag is triggered unnecessarily when an accident occurs, repair costs increase considerably.

Classification of the person: Airbag control can also be improved based on different frequencies of the heart beat in children and adults. Children have a higher pulse rate than adults. For unequivocal classification, however, other parameters should also be used, such as weight and/or height.

Monitoring the driver: Heart beat and breathing with the system according to the invention are easily-measured physiological parameters with high diagnostic value for monitoring the driver's state. The possibility for using a system of this nature is supported by the growing numbers of accidents caused by heart attack or circulatory failure while the vehicle is being driven. In addition, the heart beat could be provided together with a statement about the alertness level (attentiveness, stressability) of the driver. When a person is relaxed, the pulse rate is much lower than it is in a person who is under stress.

Long-term monitoring: This point appears not to be a motor-vehicle specific application at this time. From a medical perspective, however, it is of great benefit to monitor the driver over a longer period of time in an actual stress situation. These values could then be evaluated subsequently by a physician.

Although the present invention was described hereinabove with reference to a preferred exemplary embodiment, it is not limited thereto, but rather is capable of being modified in a diverse manner.

Finally, the features of the subclaims can be combined freely with each other and not in the order presented in the claims, provided they are independent of each other.

What is claimed is:

1. A method for the sensing of information about the position and/or movements of the body of a living being or a part of the body inside the body, comprising the following steps:
    a) sending an electromagnetic signal to a predetermined area of the body of the living being,
    b) receiving an electromagnetic signal reflected from the area of the body,
    c) evaluating the captured receive signal with regard for the difference in delay time and/or frequency relative to the transmit signal to determine the information,
    d) monitoring a range of a heart beat and breathing motion,
    e) generating a signal serving as an alarm or forwarding information to a higher-order system when evaluated information about heart and/or chest movement indicates a life-threatening, extraordinary situation, if the evaluated information falls below a selected frequency, or if the evaluated information about the heart exhibits an unusual change,
    wherein frequencies in the high-frequency range are used, wherein information obtained in evaluating of delay time differences between transmit signal and receive signal contains the distance between body or part of the body and transmit/receive antenna elements, and wherein devices for sending and receiving the signals are mounted on a steering wheel of a motor vehicle or in an immediate vicinity of the steering wheel for sensing of information about the position and/or movements of the body disposed in a motor vehicle, and emission characteristics of transmit antenna elements have an angle of aperture of less than 40 degrees.

2. The method as recited in claim 1, wherein, to sense the information about movements of the body of a living being or a part of the body inside the body, the step of evaluating the receive signal takes place by determining the Doppler frequency shift relative to the transmit signal.

3. The method as recited in claim 2, whereby, to sense the heart beat and/or breathing of the living being, a radar frequency in the range between 800 MHz and 6 GHz, and a frequency band from 100 MHz around 2.45 GHz are used, and the frequency shift is depicted in the form of information that characterizes the heart movement and/or chest movement.

4. The method as recited in claim 1, whereby the signal evaluation functions according to the mixing principle.

5. The method as recited in claim 4, whereby a further mixer is used in the signal evaluation.

6. The method as recited in claim 1, containing the step of generating a pulsed transmission signal.

7. The method as recited in claim 6, whereby the pulses are generated by switching on and off using a clock-pulse generation circuit that triggers a signal switch.

8. The method as recited in claim 6, whereby the pulses are generated by signal-filtering semiconductor elements.

9. The method as recited in claim 1, whereby, to sense the position of the body of the living being, a radar frequency in the range between 20 and 120 GHz, and a frequency band of 250 MHz around 24.5 GHz are used.

10. The method as recited in claim 1, whereby the signal evaluation of the pulsed electromagnetic receive signal functions according to the sampling principle.

11. A system for sensing information about the position and/or movements of the body of a living being or a part of the body inside the body, containing devices for carrying out the steps of the method according to claim 1.

12. The use of the method as recited in claim 1, or the system as recited in claim 11, for determining the presence and/or for monitoring a living being in a trunk of a motor vehicle, with which the devices of the system for sensing are mounted in the motor vehicle.

13. The use of the method as recited in claim 1, or the system as recited in claim 11, for one of the following purposes:
    a) detecting the presence of a person,
    b) classifying the person,
    c) monitoring the driver, or
    d) long-term monitoring,
    whereby the evaluated information about the position and/or movements of the body of a living being or a part of the body inside the body are forwarded to a higher-order system for further processing therein.

14. The method as recited in claim 1, wherein frequencies in the radar range are used.

15. The method as recited in claim 1, wherein the angle of aperture is between 20 and 30 degrees.

* * * * *